United States Patent [19]

Kesling, Jr.

[11] 4,097,524

[45] Jun. 27, 1978

[54] PROCESS FOR THE PREPARATION OF FORMAMIDES

[75] Inventor: Haven Sylvester Kesling, Jr., Drexel Hill, Pa.

[73] Assignee: Atlantic Richfield Company, Los Angeles, Calif.

[21] Appl. No.: 754,151

[22] Filed: Dec. 27, 1976

[51] Int. Cl.$^2$ .......................................... C07C 103/02
[52] U.S. Cl. ........................ 260/561 R; 260/293.86; 260/562 R; 260/557 R
[58] Field of Search ............ 260/561 R, 562 R, 557 R

[56] References Cited

U.S. PATENT DOCUMENTS

| | | | |
|---|---|---|---|
| 2,677,706 | 5/1954 | Giachino | 260/561 R |
| 2,793,211 | 5/1957 | Locicero et al. | 260/561 R |
| 3,099,689 | 7/1963 | Cragg | 260/562 R |
| 3,412,150 | 11/1968 | Nozaki | 260/561 R |
| 3,446,842 | 5/1969 | Nozaki | 260/561 R |
| 3,530,182 | 9/1970 | Haynes et al. | 260/562 R |

OTHER PUBLICATIONS

Beckwith, The Chemistry of Amides; Interscience Publishers, N.Y., N.Y., 1970, p. 118.
Saegusa et al. Tet. Letters, 1966, #49, pp. 6125–6129.
Saegusa et al., Bull. Chem. Soc. Japan 42 (1969), pp. 2610–2614.
Nefedov et al. Izv. Akad. Nauk; S.S.S.R., Ser Khim #7, 1973, pp. 1536–1550.

*Primary Examiner*—Arthur P. Demers
*Attorney, Agent, or Firm*—Coleman R. Reap

[57] ABSTRACT

A process for the preparation of formamides by reacting a tertiary amine with carbon monoxide in the presence of a solvent, a catalytic quantity of a copper salt and oxygen or an oxygen-containing gaseous mixture. The reaction is preferably carried out in the presence of excess amine, a volatile alcohol solvent, and a copper halide catalyst.

15 Claims, No Drawings

PROCESS FOR THE PREPARATION OF FORMAMIDES

BACKGROUND OF THE INVENTION

This invention relates to the preparation of formamides and, more particularly, to the preparation of formamides by the reaction of tertiary amines with carbon monoxide.

Formamides are valuable as industrial solvents and as starting materials for the preparation of important chemical intermediates and finished chemicals, such as isocyanates. Increasing interest in formamides has led to investigations for more economical and efficient processes for their production. Much recent research has been directed to the preparation of formamides by the carbonylation reaction between amines and carbon monoxide using various metal catalysts. Unfortunately, these reactions have been generally catalyzed by expensive Group VIII metal noble catalysts, such as the salts of palladium and platinum. Some success has been observed in the carbonylation of primary and secondary aliphatic and heterocyclic amines to formamides with carbon monoxide using relatively inexpensive copper salts. T. Saegusa et al, Tetrahedron Letters, Vol. 49, pp 6125-6129 (1966); T. Saegusa et al, Bull. Chem. Soc. Japan, Vol. 42, pp 2610-2614 (1969); B. Nefedov et al, Izv. Akad. Nauk. S.S.S.R. Ser Khim, No. 7, pp 1536-1540, (July 1973). U.S. Pat. No. 2,677,706 describes the preparation of formamides from mixtures of tertiary amines with primary and/or secondary amines using copper salt catalysts. This patent notes, however, that tertiary amines are unreactive when used alone. Since carbon monoxide is a very inexpensive starting material and copper salts are relatively inexpensive catalysts the preparation of formamides from tertiary amines and carbon monoxide using copper salt catalysts is potentially of considerable economic importance. Accordingly, it would be desirable to adapt this procedure to the preparation of formamides from tertiary amines.

SUMMARY OF THE INVENTION

The above-described process has been improved by this invention so that formamides can now be prepared by the reaction of carbon monoxide with tertiary amines using copper salts as catalysts. Accordingly, it is an object of the invention to present an improved method for the preparation of formamides. It is another object of the invention to present a method for preparing formamides by the reaction of carbon monoxide with tertiary amines. It is another object of the invention to present a method for producing formamides in high yields by the reaction of tertiary amines with carbon monoxide using copper salt catalysts. It is another object of the invention to present a method of preparing formamides from tertiary amines and carbon monoxide using a regenerating copper catalyst system. These and other objects of the invention will become more obvious from the following description and examples.

The above objects are achieved by carbonylating tertiary amines with carbon monoxide in the presence of an organic solvent and a small amount of oxygen or an oxygen-containing gas mixture using a copper salt catalyst. The reaction is generally carried out at a temperature in the range of about 60° to 300° C and a pressure of about 1 to 700 atmospheres. In preferred embodiments the copper salt is a copper halide, the organic solvent is a lower aliphatic alcohol, the reaction zone temperature is in the range of about 100° to 250° C, the reaction zone pressure is in the range of about 50 to 150 atmospheres, a dehydrating agent is present in the reaction zone, the reaction is carried out in the presence of excess amine and the amount of oxygen present in the reaction zone is less than the lower limit of the explosive range of mixtures of oxygen and carbon monoxide.

DESCRIPTION OF THE INVENTION

The carbonylation reaction of the invention may be carried out in any high pressure batch-type or continuous reactor. A general procedure is to charge the amine, catalyst, and the oxygen or oxygen-containing gas mixture into the reaction vessel, introduce the proper amount of carbon monoxide gas to obtain the desired reaction pressure and then heat the mixture to and maintain it at the desired temperature for the appropriate period. The reaction can be carried out batchwise or as a continuous process and the order of addition of the reactants to the reaction vessel may be varied as desired. The reaction products can be conveniently recovered and treated by any conventional method such as filtration, distillation, etc. to effect separation of the formamide from unreacted materials, catalyst, by-products, etc.

Any monofunctional or polyfunctional tertiary amine or mixture of tertiary amines having a hydrogen atom on a carbon atom adjacent to the amine nitrogen atom can be used in the process of the invention. The amine reactant has the structural formula

$$R(NR_1R_2)_n$$

wherein R, $R_1$ and $R_2$ are the same or different organic groups, usually containing up to 30 carbon atoms each, and $n$ is at least 1. R, $R_1$ and $R_2$ can be aliphatic, including cycloaliphatic, heterocyclic, or aromatic. When any one or more of R, $R_1$ and $R_2$ is aliphatic it may be saturated or unsaturated and it preferably contains up to 18 and most preferably up to 8 carbon atoms. When any one or more of R, $R_1$ and $R_2$ is aromatic it usually contains 1 to 3 condensed or non-condensed rings and is preferably mononuclear. R, $R_1$ and $R_2$ may be unsubstituted, i.e., comprised solely of carbon and hydrogen, or they may contain pendent or in-chain atoms other than carbon and hydrogen, such as oxygen, nitrogen, sulfur, the halogens, etc., or groups containing these atoms. Common atoms or groups containing these atoms include chlorine, bromine, hydroxy, ether, ester, mercaptan, thioether, thioester, amino, amido, nitro, nitroso, etc.

When $n$ is 1 the amine is monofunctional and when $n$ is greater than 1 the amine is polyfunctional. Preferred amines are those in which $n$ is 1 to 3.

If it is desired, a mixture of two or more tertiary amines may be used as the amine reactant.

Representative tertiary aliphatic and cycloaliphatic amines include trimethylamine, triethylamine, tripropylamine, tributylamine, trioctylamine, dimethylethylamine, dimethyllaurylamine, methylethyloleylamine, (3-chlorobutyl)-dimethylamine, (4-hydroxybutyl)-ethylmethylamine, N,N-dimethylcyclohexylamine, methyldicyclohexylamine, (3-nitrocyclohexyl)-dimethylamine, N-ethylpiperidine, etc.

Representative tertiary aromatic amines include di-N-alkyl substituted anilines, such as N,N-dimethylaniline, N-methyl-N-ethylaniline, di-N-alkyl substituted toluidines, such as N-N-dimethyl toluidine, di-N- substituted xylidines, such as N-methyl-N-ethylxylidine, substituted tertiary aromatic amines, such as N-methyl-N-phenyl-chloroaniline, N-methyl-N-ethyl-p-bromoaniline, N-N-dipropyl-nitroaniline, N-N-dimethyl-m-mercaptopropylaniline, the tertiary phenylene diamines, the tertiary toluene diamines, N-alkyl-N,N-diphenylamines, such as N-ethyl-N,N-diphenylamine, N-propyl-N-toluidinylaniline, N,N,N'N'-tetramethyl-4,4'-diaminodiphenylmethane, N,N-dialkyl-naphthylamines, such as N,N-dimethyl-$\beta$-naphthylamine, etc.

The preferred tertiary aliphatic amines are the saturated aliphatic amines in which each alkyl group contains up to 8 carbon atoms, such as trimethylamine, diethylpropylamine, etc. The preferred tertiary aromatic amines are the mononuclear tertiary aromatic amines, such as N,N-dimethylaniline, N-ethyl-N-methylaniline, etc.

The copper salts usable as catalysts in the process of the invention include copper(I) and copper(II) salts and mixtures of these. In general, any copper salt usable as a catalyst can be used in the invention. The copper salt anions may be inorganic, such as the halides, sulfates, sulfites, nitrates, nitrites, carbonates, etc.; or organic, such as acyl groups, including acetate, formate, propionate, alkoxides such as methoxide, ethoxide, etc.

Examples of representative copper salts are copper(I) chloride, copper(II) chloride, copper(II) bromide, copper(II) iodide, copper(II) formate, copper(II) acetate, copper(I) propionate, copper(II) methoxide, copper(I) ethoxide, etc. The preferred copper salts are the halides, particularly the copper(II) halides, such as copper(II) chloride and copper(II) bromide.

The amount of catalyst used in the reaction may vary from the minimum amount which is catalytically effective up to about 10%, based on the total weight of tertiary amine present in the reaction zone. Amounts greater than about 10% can be used, if desired, however, the efficiency of the reaction decreases as larger amounts of catalyst are employed. The amount of copper salt catalyst usually used in the process of the invention varies from about 0.01 to about 10%, and preferably from about 0.1 to about 5%, based on the total weight of tertiary amine present in the reaction zone.

A ligand or coordination complex compound of the metal catalyst can be included, if desired, in the catalyst formulation to modify the properties of the copper salt catalyst. Examples of suitable compounds include organic ligands, such as alkyl or aryl phosphines, phosphine oxides, heterocyclic amines, such as pyridine, arsines or stibines and inorganic ligands, such as tin chloride, etc. When these agents are included they are often used in amounts up to about four molar equivalents of ligand per mole of copper.

The reaction is carried out in the presence of a catalyst oxidizing agent. During the reaction between the carbon monoxide and the amine, the copper(II) ions are reduced to copper(I) ions. The oxidizing agent functions to oxidize the copper(I) back to the copper(II) state. It is not known what additional part the oxidizing agent plays in the process of the invention, but it has been discovered that tertiary amines will not react with carbon monoxide to produce formamides in the absence of an oxidizing agent, such as oxygen. Suitable oxidizing agents include oxygen or other suitable oxidizing agents, such as quinone. When oxygen is used it may be introduced as pure oxygen or as a component in a gas mixture, such as air. The amount of oxygen present in the reaction zone at any given time is preferably such that the concentration of oxygen is less than 6.1 volume percent. This is the lower limit of the explosive range of oxygen in carbon monoxide. Although the reaction can be carried out at oxygen levels of 6.1 volume percent or greater, it is preferred to keep the oxygen and carbon monoxide levels at safe concentrations to avoid the hazard of an explosion.

The reaction can be carried out with or without the use of a solvent, however, it is preferred to use a solvent. The preferred solvents are organic polar solvents especially the lower aliphatic or cycloaliphatic alcohols, i.e., those containing up to 8 carbon atoms, because they are easily separated from the product by evaporation or distillation. The most preferred solvents are the saturated aliphatic alcohols having up to 6 carbon atoms. Typical lower aliphatic and cycloaliphatic alcohols include methanol, ethanol, the propanols, the butanols, the hexanols, cyclohexanol, etc. The amount of alcohol solvent in the reaction zone is not critical, but it is usually preferred to use a sufficient quantity to completely dissolve the reactants. The optimum amounts for each reaction system can be easily determined.

Some of the alcohol may react with the tertiary amine and carbon monoxide to produce urethanes. The amount of urethane side product can be minimized by carrying out the reaction in the presence of a stoichiometric excess of tertiary amine. The excess amine serves to increase the basicity of the reaction mixture. The equivalents ratio of total amine to alcohol is usually about 2:1 to 10:1 and preferably about 2:1 to 4:1.

During the course of the reoxidation of the copper(I) salt back to a copper(II) salt, water is produced. Since water tends to poison the catalyst and causes other side reactions it is preferred to carry out the reaction under conditions such that the water formed during the reaction process is removed from the reaction zone. This can be accomplished by process techniques, such as azeotropic distillation or by using dehydrating agents in the reaction. When azeotropic distillation is employed the water can be removed with a portion of the solvent. Suitable azeotropic mixtures are those formed between alcohols and water. The use of dehydrating agents is often preferable to the use of azeotropic distillation.

The dehydrating agent can be efficiently used at concentrations ranging up to about 50%, based on the total weight of tertiary amine used. When a dehydrating is used it is preferably used at concentrations of about 25 to 50%, based on the total weight of tertiary amine present in the reaction zone. Suitable dehydrating agents include organic drying agents such as orthoesters, ketals, acetals, enolethers, trialkylorthoborates, and various inorganic drying agents, such as molecular sieves and calcium chloride. Preferred dehydrating agents are those which will release lower alcohols, i.e., aliphatic or cycloaliphatic alcohols having up to 8 carbon atoms in their structures, upon reaction with water, in a reaction similar to the following:

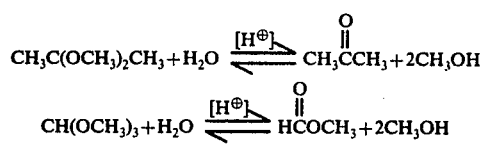

Examples of preferred dehydrating agents are trimethylorthoformate, triethylorthoformate, tributylorthoformate, 2,2-dimethoxypropane, 2,2-di-n-butoxypropane, 1,1-dimethoxycyclohexane, 1,1-di-n-butoxycyclohexane, 1,1-dimethoxymethane, 1,1-diethoxyethane, 2-ethoxyprop-2-ene, 1-methoxycyclohex-1-ene, trimethylborate. Particularly preferred dehydrating agents are the orthoesters which, when hydrolyzed with water, release alcohols having up to 6 carbon atoms in their structures. It is most preferred that the alcohol being released be the alcohol which is used as reaction solvent.

The following examples illustrate specific embodiments of the invention. Unless otherwise indicated parts and percentages are on a weight basis.

EXAMPLE I

A solution of 500 mmoles triethylamine, 53.06g (500 mmoles) trimethylorthoformate, and 60.00g of absolute methanol is charged into a 300 ml stainless steel stirred autoclave along with 25 mmoles of anhydrous copper(II) chloride. The autoclave is sealed and charged with carbon monoxide to a pressure of 1500 psig. The temperature in the autoclave is raised to and maintained at 150° C. Reaction is initiated by charging oxygen into the autoclave until the pressure reaches 1600 psig. The gas charge line is then flushed by charging carbon monoxide into the reactor until the autoclave pressure reaches 1700 psig. The reaction is permitted to proceed for two hours and then the reactor is cooled to room temperature and the contents removed. GLC (gas-liquid chromatograph) and ALC (analytical liquid chromatograph) analyses will indicate the formation of N,N-diethylformamide.

EXAMPLE II

The procedure of Example I is repeated except the N-N-diethylcyclohexylamine is substituted for the triethylamine and a mixture of anhydrous copper(II) sulfate and anhydrous copper(I) iodide is substituted for the copper chloride. GLC and ALC analyses will indicate the formation of N-cyclohexyl-N-ethylformamide.

EXAMPLE III

The procedure of Example I is repeated except that N,N-dimethylaniline is substituted for the triethylamine. GLC and ALC analyses will indicate the formation of N-methylformanilide.

EXAMPLE IV

The procedure of Example I is repeated except that N-ethylpiperidine is substituted for the triethylamine and a mixture of anhydrous copper(II) sulfate and anhydrous copper(I) iodide is substituted for the copper (II) chloride. GLC and ALC analyses will indicate the formation of piperidylformamide.

EXAMPLE V

The procedure of Example I is repeated except that ethylmethyl-(2-naphthyl)-amine is substituted for the triethylamine and a mixture of anhydrous copper(II) sulfate and anhydrous copper(I) iodide is substituted for the copper(II) chloride. GLC and ALC analyses will indicate the formation of N-ethyl-N(2-naphthyl)-formamide.

EXAMPLE VI

The procedure of Example I is repeated except that no trimethylorthoformate is added to the reaction formulation. GLC and ALC analyses will indicate the formation of N,N-diethylformamide.

EXAMPLE VII

The procedure of Example I is repeated except that the methanol is replaced by methyl acetate. GLC and ALC analyses will indicate the formation of N,N-diethylformamide.

Although the invention has been described with particular reference to specific examples, it is understood that the scope of the invention is not limited thereto but is only determined by the breadth of the appended claims.

I claim:

1. A process for the preparation of formamides which comprises reacting a tertiary aliphatic, cycloaliphatic or heterocyclic amine with carbon monoxide in the presence of a sufficient amount of a copper compound catalyst to effect the carbonylation of the amine, an agent capable of oxidizing copper and a dehydrating agent.

2. The process of claim 1 wherein the copper compound is present in an amount of about 0.01 to 10% based on the total weight of tertiary amine present.

3. The process of claim 2 wherein the copper compound is an inorganic salt.

4. The process of claim 3 wherein the copper salt is a copper halide.

5. The process of claim 4 wherein the copper halide is present in an amount of about 0.1 to 5% based on the total weight of tertiary amine present.

6. The process of claim 1 wherein the copper compound is an organic salt.

7. The process of claim 1 wherein the copper oxidizing agent is oxygen.

8. The process of claim 7 wherein the oxygen concentration in the reaction zone is less than the lower limit of the explosive range of mixtures of carbon monoxide and oxygen.

9. The process of claim 1 wherein the dehydrating agent is a member of the group consisting of orthoesters, ketals, acetals, enolethers, trialkylorthoborates, and mixtures of these.

10. The process of claim 1 wherein an organic polar solvent is present in the reaction zone.

11. The process of claim 11 wherein said organic polar solvent is an aliphatic or cycloaliphatic alcohol containing up to 8 carbon atoms.

12. A process for the preparation of formamides which comprises reacting an aliphatic, cycloaliphatic or heterocyclic tertiary amine with carbon monoxide in the presence of about 0.01 to 10%, based on the total weight of amine present, of a copper halide catalyst, oxygen in an amount less than the minimum amount which will form an explosive mixture of carbon monoxide and oxygen, a saturated aliphatic alcohol having up to 6 carbon atoms and an organic dehydrating agent selected from the group consisting of orthoesters, ketals, acetals, enolethers, trialkylorthoborates and mixtures of these, the ratio of total amine to alcohol being such that there is a stoichiometric excess of amine in the reaction zone.

13. The process of claim 12 wherein the copper halide catalyst is copper(II) chloride or copper(II) bromide and it is present in an amount of about 0.1 to 5%, based on the total weight of tertiary amine present.

14. The process of claim 12 wherein said tertiary amine is a trialkylamine.

15. The process of claim 12 wherein said dehydrating agent is an orthoester or ketal whose ester moieties have up to 6 carbon atoms.

* * * * *